United States Patent
Haidukewych et al.

(10) Patent No.: US 9,763,681 B2
(45) Date of Patent: Sep. 19, 2017

(54) ORTHOPAEDIC AIMING DEVICE FOR COMPOUND SCREW TRAJECTORIES

(71) Applicant: Biomet Manufacturing, LLC, Warsaw, IN (US)

(72) Inventors: George Haidukewych, Orlando, FL (US); Daren Granger, Warsaw, IN (US); Greg Gohring, Wabash, IN (US); Joseph O'Reilly, Granger, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 583 days.

(21) Appl. No.: 14/296,255

(22) Filed: Jun. 4, 2014

(65) Prior Publication Data

US 2015/0351821 A1    Dec. 10, 2015

(51) Int. Cl.
*A61B 17/17* (2006.01)
*A61B 17/72* (2006.01)
*A61B 17/56* (2006.01)

(52) U.S. Cl.
CPC .......... *A61B 17/1725* (2013.01); *A61B 17/72* (2013.01); *A61B 2017/564* (2013.01)

(58) Field of Classification Search
CPC ........................... A61B 17/1725; A61B 17/72
See application file for complete search history.

(56) References Cited

U.S. PATENT DOCUMENTS

| | | | |
|---|---|---|---|
| 5,620,449 A * | 4/1997 | Faccioli | A61B 17/1725 606/96 |
| 6,039,739 A | 3/2000 | Simon | |
| 7,169,149 B1 * | 1/2007 | Hajianpour | A61B 17/72 606/54 |
| 7,588,577 B2 * | 9/2009 | Fencl | A61B 17/1659 606/104 |
| 8,273,092 B2 | 9/2012 | Sasing et al. | |
| 8,568,421 B2 | 10/2013 | Johnstone | |
| 8,617,166 B2 * | 12/2013 | Hanson | A61B 17/1764 606/86 R |

* cited by examiner

*Primary Examiner* — Andrew Yang
(74) *Attorney, Agent, or Firm* — Schwegman Lundberg & Woessner, P.A.

(57) ABSTRACT

An orthopaedic aiming device system is provided that includes a targeting device. The targeting device has a curved portion with an end and at least one guide opening formed therethrough. The curved portion also defines an arced axis. Connected to the end of the curved portion is a mounting portion that has at least one mounting opening formed therethrough. The mounting opening defines a mounting axis that is approximately orthogonal to at least one point on the arced axis of the curved portion. The orthopaedic aiming device system can also include mounting pins, a positioning device, and an orthopaedic implant. The mounting pins can include distancing features that interact with distance locking features of the mounting opening(s) to properly distance the targeting device from the orthopaedic implant. Also included is a method to target implant openings that have compound angled screw trajectories using an orthopaedic aiming device system.

17 Claims, 5 Drawing Sheets

ORTHOPAEDIC AIMING DEVICE FOR COMPOUND SCREW TRAJECTORIES

BACKGROUND OF THE INVENTION

1. Field of the Invention

The present invention relates to aiming devices, and, more particularly, to aiming devices for medical implants.

2. Description of the Related Art

Aiming devices, such as jigs, are known in the art for aligning openings on orthopaedic implants with devices, such as bone screws, to affix bone fragments to the orthopaedic implants. The use of a jig allows for a user to insert the bone screws into a patient without the need for fully exposing the bone during surgery. The jig is typically connected to an end of the orthopaedic implant closest to an incision, with openings formed on the jig aligning with respective openings formed in the implant. To ensure proper alignment of the jig openings with the implant openings, an imaging technique such as fluoroscopy can be used to help adjust the jig until it is properly aligned. Once the jig is properly aligned, the bone screws can be passed through the jig openings and attached to their respective implant openings.

Most jigs in use today are designed to be used in conjunction with orthopaedic implants that have simple angle screw trajectories, i.e., the implant openings are not angled relative to both the x-axis and y-axis of the implant. Such trajectories are relatively simple to align with known jigs.

However, some orthopaedic implant devices incorporate compound angled screw trajectories, i.e., the implant openings are angled relative to both the x-axis and y-axis of the implant. Implants with compound angled screw trajectories have seen more widespread use due to evolving surgical techniques and the benefits that have been realized by using compound angled screw trajectories, such as compensation for various fracture patterns and good bone purchase. Such compound angled screw trajectory implants cannot be targeted with traditional jig devices for a variety of reasons, including difficulty of aligning the jig openings with the implant openings. While fluoroscopy alone has been used to target implants with compound angled screw trajectories, this targeting technique is not always feasible due to difficulty, time constraints, costs, and the risk of exposing the patient and surgical team to excessive radiation.

What is needed in the art is a more effective targeting device for targeting implants with compound screw trajectories.

SUMMARY OF THE INVENTION

The present invention provides an orthopaedic aiming system that includes a targeting device with a curved portion and a mounting portion that have openings formed therethrough to allow effective targeting of orthopaedic implants with compound angled screw trajectories.

The invention in one form is directed to an orthopaedic aiming device system that includes a targeting device having a curved portion and a mounting portion. The curved portion has an end and at least one guide opening is formed through the curved portion. The curved portion defines an arced axis. The mounting portion is connected to the end of the curved portion and there is at least one mounting opening formed through the mounting portion that defines a mounting axis. The mounting axis is approximately orthogonal to at least one point on the arced axis. The orthopaedic aiming device system can also include an orthopaedic implant connected to the targeting device. The orthopaedic implant has a first end, a second end, and a plurality of implant openings, and defines a transverse plane. At least one mounting pin connects the mounting portion of the targeting device to the second end of the orthopaedic implant through the at least one mounting opening and one of the plurality of implant openings in the transverse plane.

The invention in another form is directed to a method for targeting implants that have compound angled screw trajectories. The method includes providing an orthopaedic implant that has a plurality of implant openings and defining a transverse plane. At least one of the implant openings has a simple angled screw trajectory and lies on the transverse plane and at least one of the implant openings has a compound angled screw trajectory. The orthopaedic implant is implanted within a patient. The transverse plane is aligned with a medial-lateral plane of the patient. Also provided is a targeting device that includes a curved portion and a mounting portion. The curved portion has an end and at least one guide opening formed therethrough. The curved portion defines an arced axis. The mounting portion is connected to the end of the curved portion and has at least one mounting portion formed therethrough that defines a mounting axis which is approximately orthogonal to at least one point on the arced axis. At least one mounting pin is connected to the orthopaedic implant through at least one of the implant openings along the transverse plane and placing the mounting pin at least partly within a mounting opening of the targeting device.

An advantage of the present invention is that it provides a traditional aiming device approach to inserting screws into orthopaedic implant openings with non-traditional compound angled screw trajectories at a distal end of the orthopaedic implant.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
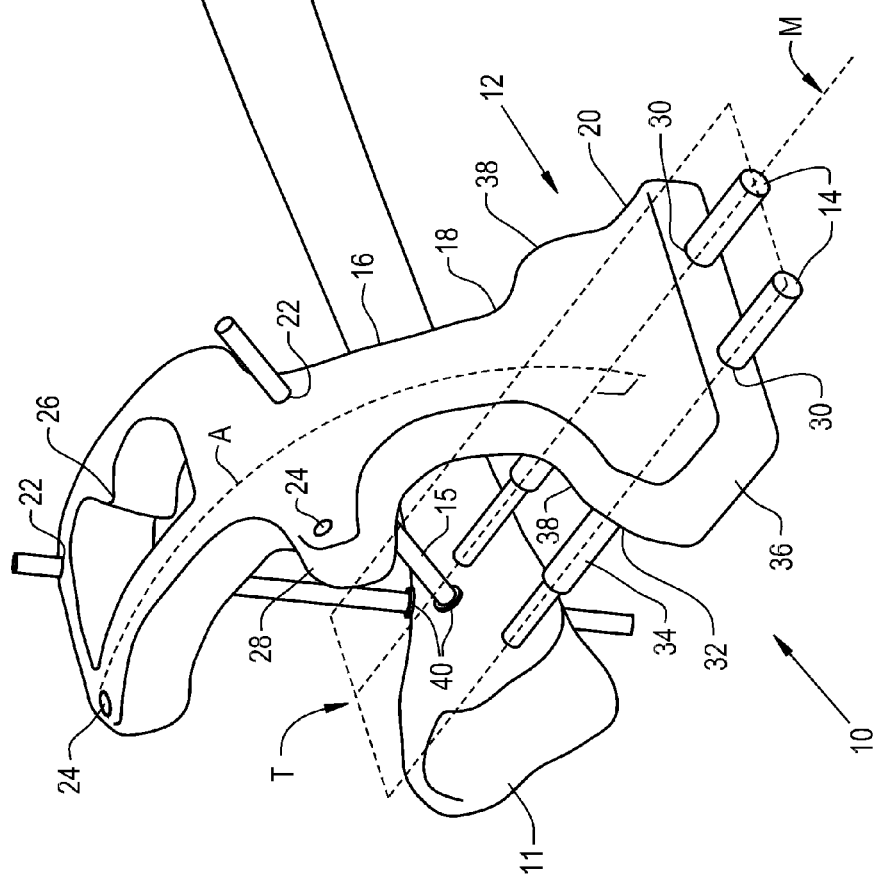
FIG. 1 is a perspective view of an embodiment of the present invention in use.
Figure 2:
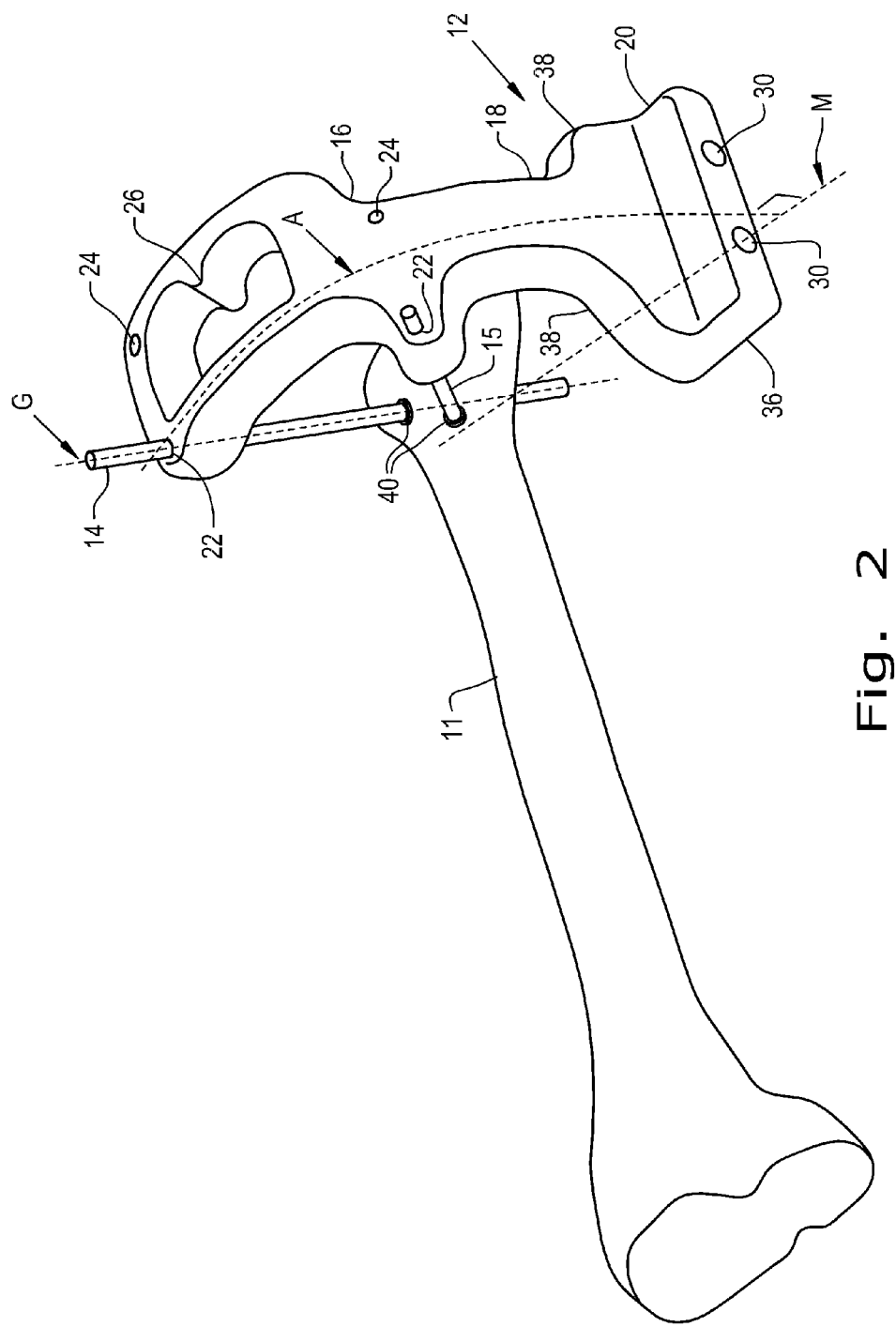
FIG. 2 is another perspective view of an embodiment of the present invention in use.

Referring now to the drawings, and more particularly to FIGS. 1 and 2, there is shown an orthopaedic aiming device system 10 which generally includes a targeting device 12, mounting pins 14 and an orthopaedic implant (not seen). The orthopaedic implant has already been implanted into an anatomy structure 11, in this case a bone, of a patient and defines a transverse plane T that overlaps the patient's medial-lateral plane. The mounting pins 14 are connecting the targeting device 12 to the orthopaedic implant. While it can't be seen in FIGS. 1 and 2, the orthopaedic implant can have multiple implant openings formed therethrough. The location of the implant openings correlate to the positions of the mounting pins 14 connecting the targeting device 12 to the orthopaedic implant. As shown by the positioning of mounting pin 15, at least one of the implant openings formed through the orthopaedic implant has a compound angled screw trajectory, and at least one of the implant openings has a simple angled screw trajectory and is located on the transverse plane T.

The targeting device 12 has a curved portion 16 with an end 18 connected to a mounting portion 20. The curved portion 16 follows an arc shape that defines an arced axis A therethrough. The curved portion 16 has a length that can vary, depending on the intended use of the targeting device 12 and positioning of target sites. Formed through the curved portion 16 is at least one guide opening 22, 24, although there could be many guide openings 22, 24 formed through the curved portion 16. The guide openings 22, 24 are sized to allow a variety of surgical tools and implantable devices to pass through, e.g., drill guides, drill components, bone screws. The guide openings 22, 24 can be formed through the curved portion 16 to correspond to the position of targets on an orthopaedic implant, such as implant openings, or other target sites in the patient's anatomy. At least one of the guide openings 22, 24 defines a guide axis G, although there can be multiple guide axes corresponding to the multiple guide openings 22, 24. The guide axis G can be perpendicular or angled relative to the arc axis A, depending on the targeting device's intended target's geometry. If there are multiple guide openings 22, each guide opening 22 can have a corresponding guide opening 24 that is co-axially perpendicular relative to the arc axis A. Such a configuration allows for the targeting device 12 to be used at mirror anatomical locations, such as a left and right leg of a patient (as shown in FIGS. 1 and 2). A viewing window 26 can be formed through the curved portion 16 which allows the target device's user to view an area through the viewing window 26. The viewing window 26 can also be added to reduce the amount of material in the targeting device 12, reducing the weight, as well as adjust the weight distribution of the targeting device 12 to allow for easier handling of the targeting device 12 during use. Handle portions 28 can also be formed on the curved portion 16 to provide an ergonomic gripping surface for the targeting device's user.

The curved portion 16 has an end 18 that is connected to a mounting portion 20. The mounting portion 20 has at least one mounting opening 30, which defines a mounting axis M that is generally orthogonal relative to at least one point on the arced axis A. The mounting opening 30 is sized to allow a portion of a mounting pin 14 to go through the mounting opening 30. A distance locking feature 32 can be formed within or on the mounting opening 30 to interact with features 34 formed on a mounting pin 14 to keep the targeting device 12 the correct distance from the orthopaedic implant, which helps align the guide openings 22, 24 on the curved portion 16 with the implant openings on the orthopaedic implant. The distance locking feature 32 can be any type of structural feature that can act as a stop for the feature 34 formed on the mounting pin 14. The distance locking feature 32 could be, for example, the mounting opening 30 having a smaller diameter than the feature 34 of the mounting pin 14, which prevents the mounting pin 14 from advancing within the mounting opening 30 when the feature 34 abuts the distance locking feature 32. Other, more elaborate features that can act as the distance locking feature 32 within or on the mounting opening 30 are known in the art, and can be suitable for use in the present invention. While the mounting portion 20 shown in FIGS. 1 and 2 is shaped as a mostly rectangular prism base 36 with a pair of rounded portions 38 converging along the base's length at the curved portion 16, the mounting portion's 20 shape can be adjusted to fulfill various design objectives such as ergonomics and weight distribution.

Although the targeting device 12 of FIGS. 1 and 2 is shown as a single body, the curved portion 16 and the mounting portion 20 could be separable to provide adjustable targeting devices. Materials for construction of the targeting device 12 and its components should generally be suitable for use in environments where contact with biological fluids will occur. Such materials include carbon fiber and biocompatible polymers and metals, with methods of fabricating shapes of such materials known in the art. The targeting device 12 can be designed to either be sterilized after each use or as a disposable unit.

Mounting pins 14 are utilized to keep the targeting device 12 properly positioned relative to the orthopaedic implant and to prevent the targeting device's 12 position from shifting while fixation devices, such as bone screws, are being inserted into the implant openings. The mounting pins 14 are sized to fit at least partly within the mounting opening(s) 30 and implant openings. The mounting pins 14 are generally cylindrical in shape, but this can be adjusted as desired. The mounting pin(s) 14 can have a threaded end (not shown) that is threaded into a corresponding threaded implant opening 40 of the orthopaedic implant to lock the mounting pin(s) 14 into place. A distancing feature 34 can be formed on each mounting pin 14 to interact with the distance locking features 32 to stop the targeting device 12 in position and help keep the targeting device 12 properly aligned with the orthopaedic implant. The distancing feature 34 can be as simple as an enlarged diameter along a portion of the mounting pin 14 that prevents the mounting pin 14 from going past the mounting opening's diameter (the distance locking feature 32). As previously discussed, other such complementary distance locking features 34 are known that could be suitably used as well. The mounting pin(s) 14 can be formed from any material suitable to give the strength and biocompatibility necessary for holding the targeting device 12 in place during orthopaedic surgery, such as titanium and biocompatible polymers.

To use the orthopaedic aiming device system 10 shown in FIGS. 1 and 2, the orthopaedic implant is first inserted into an anatomical location 11, shown as an intramedullary canal of a patient's tibia. Once the orthopaedic implant is inserted in the intramedullary canal, an image can be captured with fluoroscopy to ensure that the implant openings are properly oriented relative to the tibia. Proper orientation of the orthopaedic implant will have at least one implant opening of the orthopaedic implant lying on the patient's medial-lateral plane, which corresponds to a transverse plane T of the implant. Another fluoroscopy image can be taken to locate the implant opening on the transverse plane T, and a drill can be aligned with this implant opening. When the drill is aligned with this implant opening, the drill is activated and driven toward the implant opening, forming a path through the patient's anatomy to the implant opening in order to insert a mounting pin 14 at least partly into the implant opening. A mounting pin 14 is then passed through the path to the implant opening, and can be locked along the transverse plane T into the implant opening. Once the mounting pin 14 is locked in place with the implant opening, another mounting pin 14 can optionally be locked into another implant opening using a similar method. After the mounting pin(s) 14 are locked into the orthopaedic implant, the targeting device's 12 mounting opening(s) 30 can slide over the mounting pin(s) 14 until a distance locking feature 32 of the mounting opening(s) 30 interacts with a distancing feature 34 of the mounting pin(s) 14, preventing further advancing of the targeting device 12 along the mounting pin(s) 14 and/or locking the targeting device 12 into place. At this point, the targeting device 12 should be properly positioned relative to the orthopaedic implant, and bone screws for fixation within the implant can be inserted into remaining implant openings of the orthopaedic implant. The bone screws are targeted to the remaining implant openings by the guide openings 22, 24 formed through the curved portion 16 of the targeting device 12. As the guide openings 22, 24 on the curved portion 16 are angled to correspond to the compound angled screw trajectories of the implant openings, the bone screws can be fixated within the orthopaedic implant using known techniques.

Figure 3:
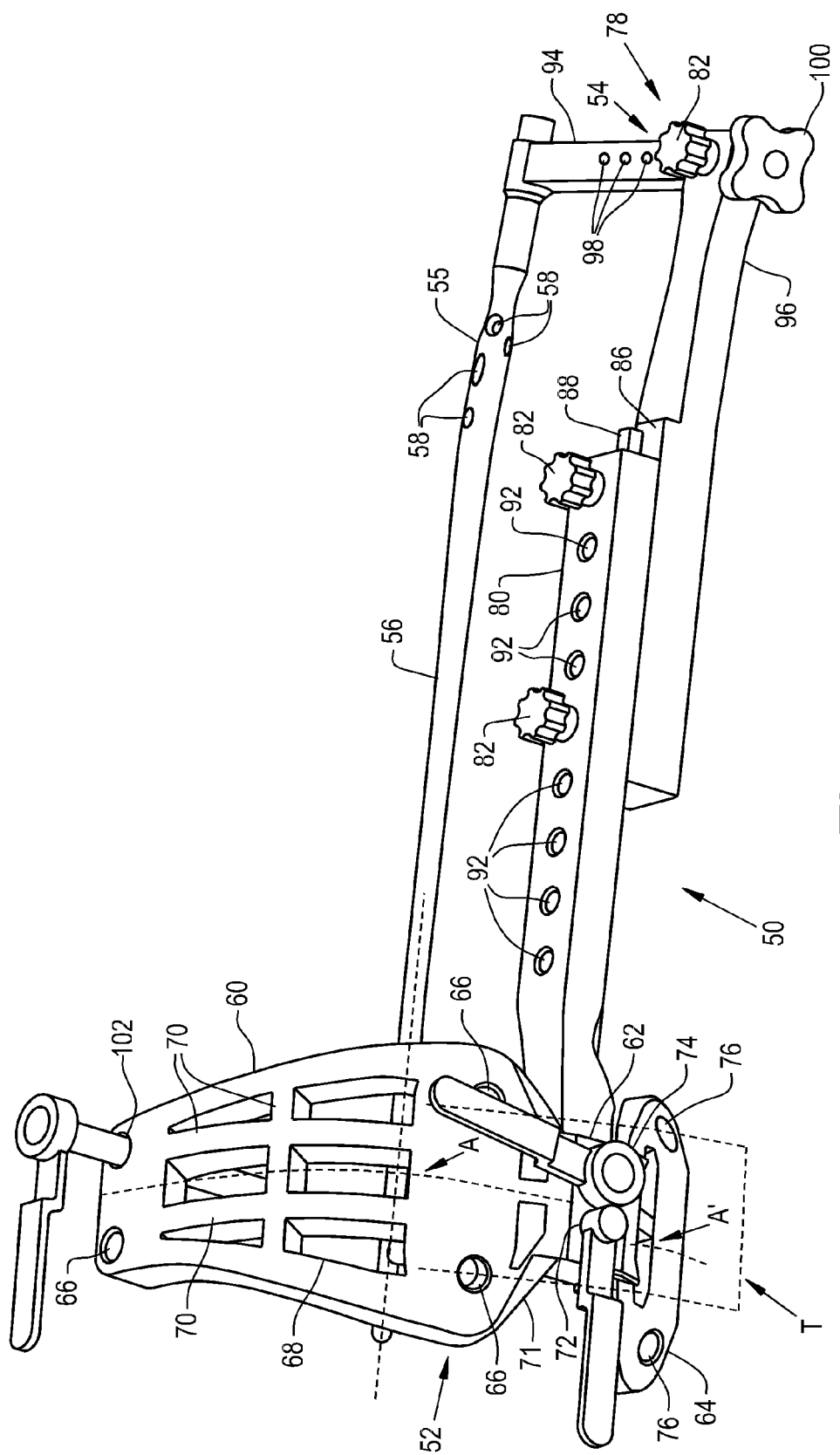
FIG. 3 is a perspective view of another embodiment of the present invention.
Figure 4:
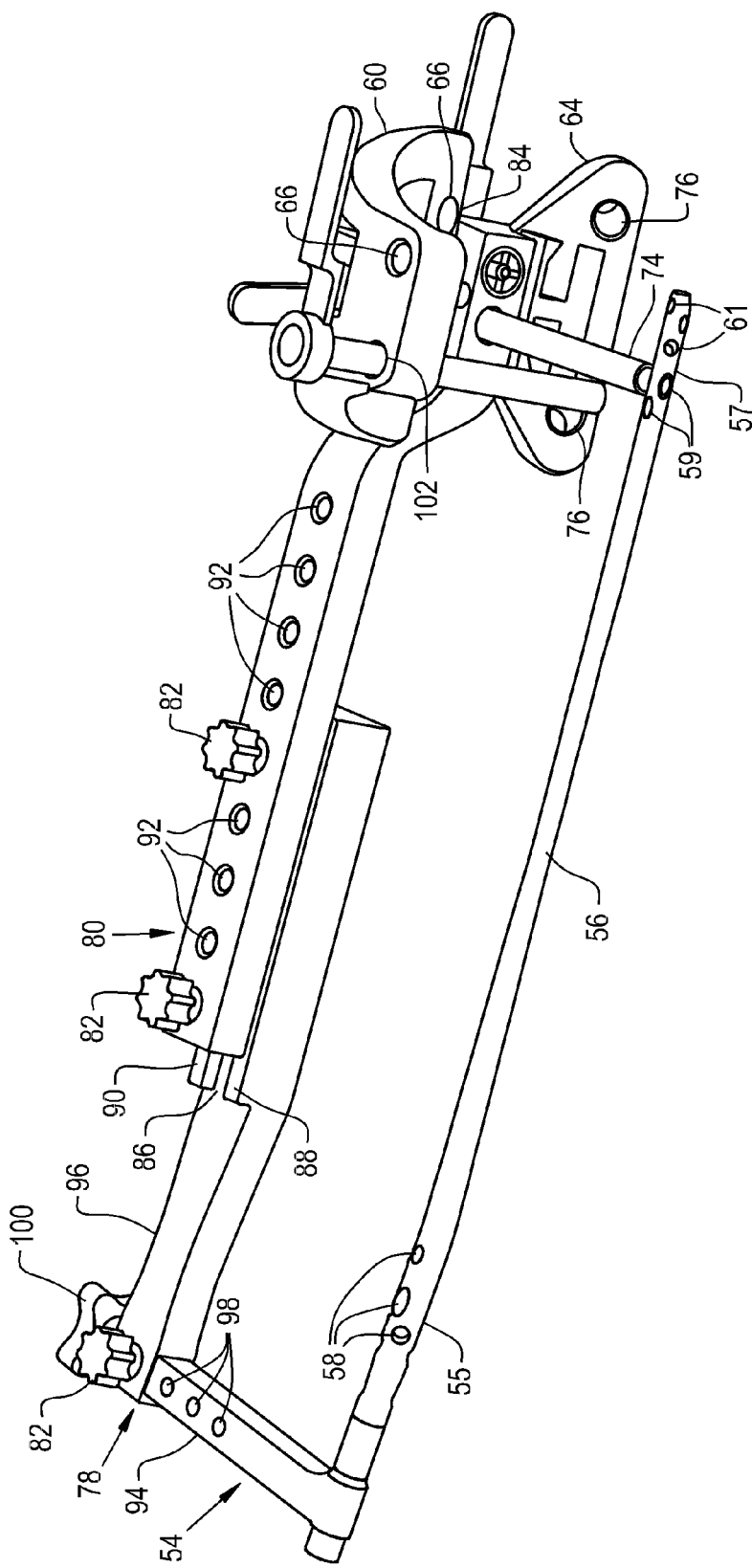
FIG. 4 is another perspective view of the embodiment of the present invention shown in FIG. 3.
Figure 5:
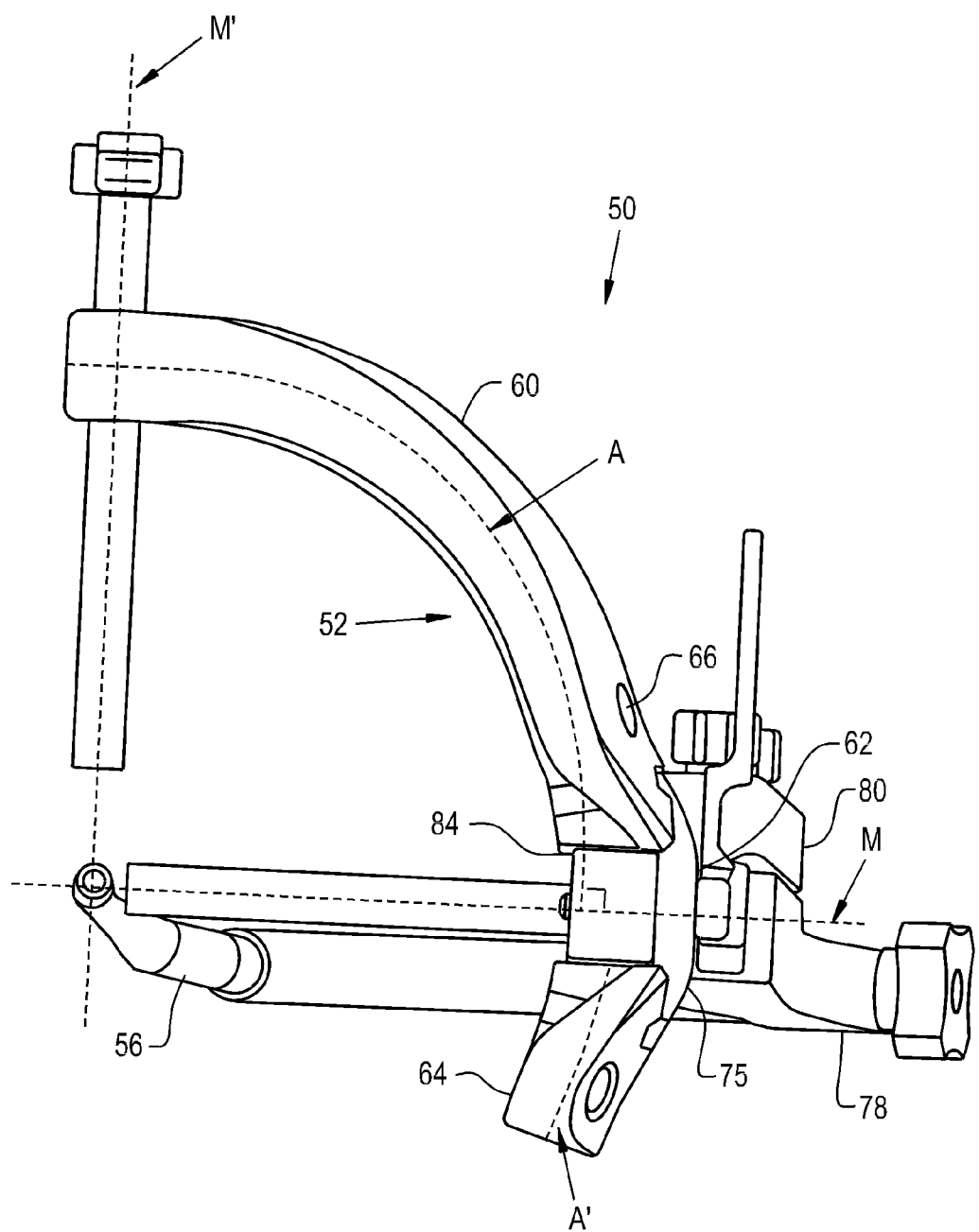
FIG. 5 is yet another perspective view of the embodiment of the present invention shown in FIGS. 3 and 4.

Referring now to FIGS. 3-5, another embodiment of an orthopaedic aiming device system 50 is shown that includes a targeting device 52, a positioning device 54 and an orthopaedic implant 56. The orthopaedic implant 56 shown can be one with the same design as shown in FIGS. 1 and 2, or can have a different geometry and arrangement of implant openings 58, 59, 61. The orthopaedic implant 56 has a first end 55 and a second end 57. The orthopaedic implant 56 defines a transverse plane T that would correspond to a patient's medial-lateral plane when implanted, and at least one of the implant openings 59 is located on the transverse plane T at the second end 57. For illustrative purposes, the orthopaedic implant 56 in FIGS. 3-5 is shown outside of a patient, but would normally be implanted within an anatomy feature of the patient.

As can be seen, the targeting device 52 has a curved portion 60, a mounting portion 62, and an additional curved portion 64. The curved portion 60 of the targeting device 52 shown in FIGS. 3-5 is similar to the curved portion 16 of the targeting device 12 shown in FIGS. 1 and 2 and defines an arced axis A. The curved portion 60 includes guide openings 66 angled relative to the arced axis A and placed to correspond to implant openings 58 on the orthopaedic implant 56. The implant openings 58 can be implant openings with simple angle screw trajectories 59 or implant openings with compound angled screw trajectories 61. As can be seen in FIG. 3, a viewing window 68 is formed that has window bars 70 being formed from one side of the viewing window 68 to another. The window bars 70 can be formed to add structural rigidity to the curved portion 60 when the viewing window 68 is desired to lower the weight and/or provide the user vision of the surgical area. Although not shown in FIGS. 3-5, the curved portion 60 can also include handle portions similar to those shown in FIGS. 1-2.

The curved portion 60 has an end 71 that is connected to a mounting portion 62. The mounting portion 62 has one or more mounting openings 72 that allow for mounting pins (not shown) to be inserted through in order to connect the targeting device 52 to the orthopaedic implant 56 and hold the targeting device 52 in place relative to the orthopaedic implant 56. The mounting openings 72 can be sized to allow a drill guide 74 to pass through, as well as mounting pins and fixation devices such as bone screws. At least one of the mounting openings 72 defines a mounting axis M (shown in FIG. 5), which is approximately orthogonal to at least one point on the arced axis A and corresponds to an implant opening 59 at the second end 57 of the orthopaedic implant 56 that lies in the transverse plane T. The mounting portion 62 can also include a groove 84 (shown in FIGS. 4 and 5) that allows for the targeting device 52 to be connected to the positioning device 54.

The mounting portion 62 has an end 75 that is connected to another curved portion 64. This other curved portion 64 defines another arced axis A' that can be the same shape as the arced axis A of the curved portion 60 or have a different shape. The other curved portion 64 also has guide openings 76 formed therethrough that are angled relative to the other arced axis A' and placed in order to align with implant openings 61 that have compound angled screw trajectories. This other curved portion 64 can be added to target implant openings 61 that would require the curved portion 60 having an undesirable length, position and/or angle to align with the target.

A positioning device 54 is connected to the first end 55 of the orthopaedic implant 56 and the targeting device 52. The positioning device 54 can be a traditional jig that is known in the art. As can be seen in FIGS. 3 and 4, the positioning device 54 has a first portion 78 that is connected to the first end 55 of orthopaedic implant 56 and a second portion 80 that is connected to the targeting device 52. The first portion 78 of the positioning device 54 acts as a spacer between the targeting device 52 and the orthopaedic implant 56 along the transverse plane T and can also provide stability to the targeting device 52 while targeting screws to the orthopaedic implant 56. The second portion 80 can be connected to the first portion 78 by threaded locking pins 82 and fit into a groove 84 formed in the mounting portion 62 of the targeting device 52 and locked into place to connect the targeting device 52 to the first portion 78. The first portion 78 can have a portion with a track 86 formed thereon. The track 86 can interact with a protrusion (not shown) formed on the second member 80 to controllably slide along the track 86. The first portion 78 can also have threaded locking openings (not shown) formed between two rails 88, 90 of the track 86 that correspond to pin openings 92 formed on the second portion 80. The pin openings 92 of the second portion 80 can be aligned with locking openings on the first portion 78, and then have threaded locking pins 82 inserted through the pin openings 92 and twisted within the threaded locking openings to lock the second portion 80, and targeting device 52, in place relative to the first portion 78. This configuration allows the targeting device 52 to target implant openings at the second end of orthopaedic implants with varying lengths, without the need for several different positioning devices. If desired, the first portion 78 can be split into a base 94 that is statically connected to the orthopaedic implant 56 and a slideable section 96 which connects to the second portion 80 (connected to the targeting device 52) and can translate along the base 94 in a direction that is orthogonal to a longitudinal axis of the orthopaedic implant 56. This configuration enables the positioning device 54 to be used in surgeries involving patients of varying size. The slideable section 96 fits over the base 94 with sufficient clearance to allow the slideable section 96 to slide along the base 94. A threaded locking pin 82 placed through an opening (not shown) on the slideable section 96 can lock into threaded openings 98 on the base 94 to allow for the slideable section 96 to lock to the base 94. Movement of the slideable section 96 along the base 94 therefore adjusts the position of the targeting device 52 relative to the orthopaedic implant 56 similarly to the distancing feature 34 previously described.

A stop 100 can be placed on the base 94 to limit the distance that the slideable section 96 can slide along the base 94.

When a positioning device 54 is being used to help align the targeting device 52 to target implant openings 58, 59, 61 in the orthopaedic implant 56, it can be useful to have a secondary mounting opening 102 through the curved portion 60 of the targeting device 52 that defines a secondary mounting axis M' that is perpendicular to the mounting axis M defined through the mounting portion 62 and corresponds to one of the implant openings 59 on the orthopaedic implant 56, as seen in FIG. 5. By having a secondary mounting opening 102 targeted to one of the implant openings 59, the targeting device 52 can be secured in all 3 dimensions by the mounting pins and positioning device 54 to provide stability and prevent translation and rotation along the X, Y or Z axis. Such a configuration also allows for more versatility in the techniques that can be used to target screws to the implant openings 58, 59, 61 of the orthopaedic implant 56.

When the orthopaedic aiming device system 50 shown in FIGS. 3-5 is chosen to target screws to implant openings 59, 61 at the second end 57 of the orthopaedic implant 56, the procedure to align the targeting device 52 slightly differs from that used to align the targeting device 12 shown in FIGS. 1-2. To use the orthopaedic aiming device system 50, the orthopaedic implant 56 is first implanted into a patient's anatomy, such as a tibia. Fluoroscopy can then be used to capture an image of the orthopaedic implant 56 and its implant openings 58, 59, 61 relative to the tibia. The orthopaedic implant 56 can be adjusted so that at least one of the implant openings 59 at the second end 57 lies on the transverse plane T that corresponds to the patient's medial-lateral plane. Once the orthopaedic implant 56 is properly positioned within the tibia, the first portion 78 of the positioning device 54 is connected to a first end 55 of the orthopaedic implant 56. The second portion 80 of the positioning device 54 can be pre-connected to the first portion 78, or can be connected to the targeting device 52 through the groove 84 and then connected to the first portion 78 using the threaded locking pins 82 disposed through pin openings 92. Once the targeting device 52 is connected to the first portion 78 via the second portion 80, drill guide 74 can be inserted through mounting opening(s) 76, 102 to direct a drill that forms a path to implant openings 59. Once the path is formed, mounting pin(s) can be inserted through mounting opening(s) 76, 102 and locked into place with implant opening(s) 59 at a second end 57 of the orthopaedic implant 56 to further secure the targeting device 52 in place. At this point, the targeting device's 52 guide openings 66, 76 should be properly aligned with the orthopaedic implant's 56 implant openings 59, 61 at the second end 57. Traditional techniques to insert bone screws into the implant openings 58, 59, 61 can then be used to seat the bone screws in the implant openings 58, 59, 61 through the guide openings 66, 76.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic aiming device system, comprising:
    a targeting device, including:
        a curved portion with an end, a top surface, a bottom surface, and a first plurality of guide openings disposed therein that extend from the top surface to the bottom surface, said curved portion defining an arced axis, each of said first plurality of guide openings defining a guide axis that is perpendicular to the arced axis, wherein at least two first guide openings have guide axes that intersect to form an acute angle;
        a mounting portion connected to said end, said mounting portion having at least one mounting opening formed therethrough that defines a mounting axis, said mounting axis being approximately orthogonal to at least one point on said arced axis;
    at least one mounting pin at least partly disposed through at least one of said at least one mounting opening and said at least one guide opening, wherein the at least one mounting pin comprises a distancing feature; and
    an orthopaedic implant connected to said at least one mounting pin and having a first end, a second end and a plurality of implant openings, said orthopaedic implant defining a transverse plane and said second end connecting to said at least one mounting pin at least partly through one of said plurality of implant openings within said transverse plane.

2. The orthopaedic aiming device system according to claim 1, wherein said targeting device has a viewing window formed therethrough.

3. The orthopaedic aiming device system according to claim 1, wherein said distancing feature is at least one of an enlarged diameter, a locking pin, a threading and a taper.

4. The orthopaedic aiming device system according to claim 3, wherein said at least one mounting opening has a distance locking feature configured to interact with said distancing feature of said at least one mounting pin.

5. The orthopaedic aiming device system according to claim 4, wherein said distance locking feature is configured to prevent movement of said distancing feature past said distance locking feature.

6. The orthopaedic aiming device system according to claim 2, further comprising a corresponding second plurality of guide openings that is laterally spaced apart from said first plurality of guide openings relative to the arced axis.

7. The orthopaedic aiming device system according to claim 1, wherein at least one of said plurality of implant openings forms an acute angle relative to said at least one mounting pin.

8. The orthopaedic aiming device system according to claim 1, wherein at least one of said first plurality of guide openings defines a guide axis that is orthogonal to said mounting axis.

9. The orthopaedic aiming device system according to claim 7, further comprising:
    a positioning device connecting said first end to said targeting device and having a first portion and a second portion, said first portion connected to said first end and said second portion connected to said targeting device.

10. The orthopaedic aiming device system according to claim 9, wherein said second portion is configured to allow movement of said targeting device relative to said orthopaedic implant along at least one axis.

11. A method of aligning an aiming device with an orthopaedic implant, the method comprising the steps of:
    obtaining or providing an orthopaedic implant including a plurality of implant openings and defining a transverse plane, at least one of said plurality of implant openings having a simple angled screw trajectory on the transverse plane and at least one of said plurality of implant openings having a compound angled screw trajectory;

implanting said orthopaedic implant within a patient;

aligning the transverse plane with a medial-lateral plane of the patient;

obtaining or providing a targeting device including:

a curved portion with an end, a top surface, a bottom surface, and a first plurality of guide openings disposed therein that extend from the top surface to the bottom surface, said curved portion defining an arced axis, each of said first plurality of guide openings defining a guide axis that is perpendicular to the arced axis, wherein at least two first guide openings have guide axes that intersect to form an acute angle, wherein at least one of said plurality of guide openings corresponds to said at least one of said plurality of implant openings having a compound angled screw trajectory; and a mounting portion connected to said end, said mounting portion having at least one mounting opening formed therethrough that defines a mounting axis, said mounting axis being approximately orthogonal to at least one point on said arced axis;

connecting at least one mounting pin to said orthopaedic implant through at least one of said plurality of implant openings along the transverse plane; and placing said at least one mounting pin at least partly within said at least one mounting opening.

12. The method according to claim 11, further comprising the steps of:

imaging an area around said orthopaedic implant;

identifying a location of the transverse plane relative to said targeting device; and creating a path through the patient to at least one of said implant openings after said imaging step.

13. The method according to claim 12, wherein said curved portion includes another mounting opening defining another mounting axis, said other mounting axis being perpendicular to said mounting axis.

14. The method according to claim 13, further comprising the step of connecting a mounting pin to one of said plurality of implant openings through said other mounting opening.

15. The method according to claim 11, wherein said aiming device includes a viewing window formed in said aiming body.

16. The method according to claim 11, further comprising the step of connecting said targeting device to a positioning device.

17. The method according to claim 16, further comprising the step of adjusting a position of said targeting device along at least one axis using said positioning device.

* * * * *